(12) United States Patent
Cochet et al.

(10) Patent No.: US 8,829,162 B2
(45) Date of Patent: Sep. 9, 2014

(54) IN VITRO METHOD FOR DIAGNOSING PROSTATE CANCER

(75) Inventors: Claude Cochet, Claix (FR); Odile Filhol, Claix (FR); Mathieu Laramas, Meylan (FR)

(73) Assignees: Inserm (Institut National de la Sante et de la Recherche Medicale), Paris Cedex (FR); Commissariat a l'Energie Atomique, Paris (FR)

( * ) Notice: Subject to any disclaimer, the term of this patent is extended or adjusted under 35 U.S.C. 154(b) by 845 days.

(21) Appl. No.: 12/522,290

(22) PCT Filed: Jan. 2, 2008

(86) PCT No.: PCT/EP2008/050004
§ 371 (c)(1),
(2), (4) Date: Jul. 7, 2009

(87) PCT Pub. No.: WO2008/083998
PCT Pub. Date: Jul. 17, 2008

(65) Prior Publication Data
US 2010/0136576 A1    Jun. 3, 2010

(30) Foreign Application Priority Data
Jan. 10, 2007 (EP) ................... 07290032

(51) Int. Cl.
*C07K 16/00* (2006.01)
*G01N 33/53* (2006.01)
*C07K 16/30* (2006.01)
*C07K 16/40* (2006.01)
*G01N 33/574* (2006.01)

(52) U.S. Cl.
CPC ............. *C07K 16/40* (2013.01); *C07K 16/3069* (2013.01); *G01N 2333/9121* (2013.01); *G01N 33/57434* (2013.01)
USPC .................. 530/387.1; 530/388.1; 530/391.3; 435/7.1

(58) Field of Classification Search
None
See application file for complete search history.

(56) References Cited

U.S. PATENT DOCUMENTS

2008/0286814 A1* 11/2008 Lopez et al. ................. 435/7.23

OTHER PUBLICATIONS

Paul, Fundamental Immunology, 3rd Edition, 1993, pp. 292-295, under the heading Fv Structure and Diversity in Three Dimensions.*
Rudikoff et al, Proc. Natl. Acad. Sci. USA, 79(6):1979-1983, Mar. 1982.*
MacCallum et al, J. Mol. Biol., 262, 732-745, 1996.*
Coleman P. M., Research in Immunology, 145:33-36, 1994.*
Ahmed et al., Trends Cell Biol., 12(5):226-230 (2002).
Faust et al., Int. J. Biochem. Cell Biol., 31:941-949 (1999).
Landesman-Bollag et al., Oncogene, 20:3247-3257 (2001).
Laramas et al., Eur. J. Cancer, 43:928-934 (2007).
Munstermann et al., Eur. J. Biochem., 189:251-257 (1990).
O-charoenrat et al., Clin. Cancer Res., 10:5792-5803 (2004).
Wang et al., J. Cell. Biochem., 99:382-391 (2006).
Yenice et al., The Prostate, 24:11-16 (1994).

* cited by examiner

*Primary Examiner* — Mark Halvorson
(74) *Attorney, Agent, or Firm* — McAndrews, Held & Malloy Ltd.

(57) ABSTRACT

The invention relates to an in vitro method for diagnosing prostate cancer and to antibodies and fragments thereof directed against CK2-α and their use for the diagnosis and prognosis of prostate cancer.

10 Claims, 3 Drawing Sheets

US 8,829,162 B2

IN VITRO METHOD FOR DIAGNOSING PROSTATE CANCER

Figure 1:
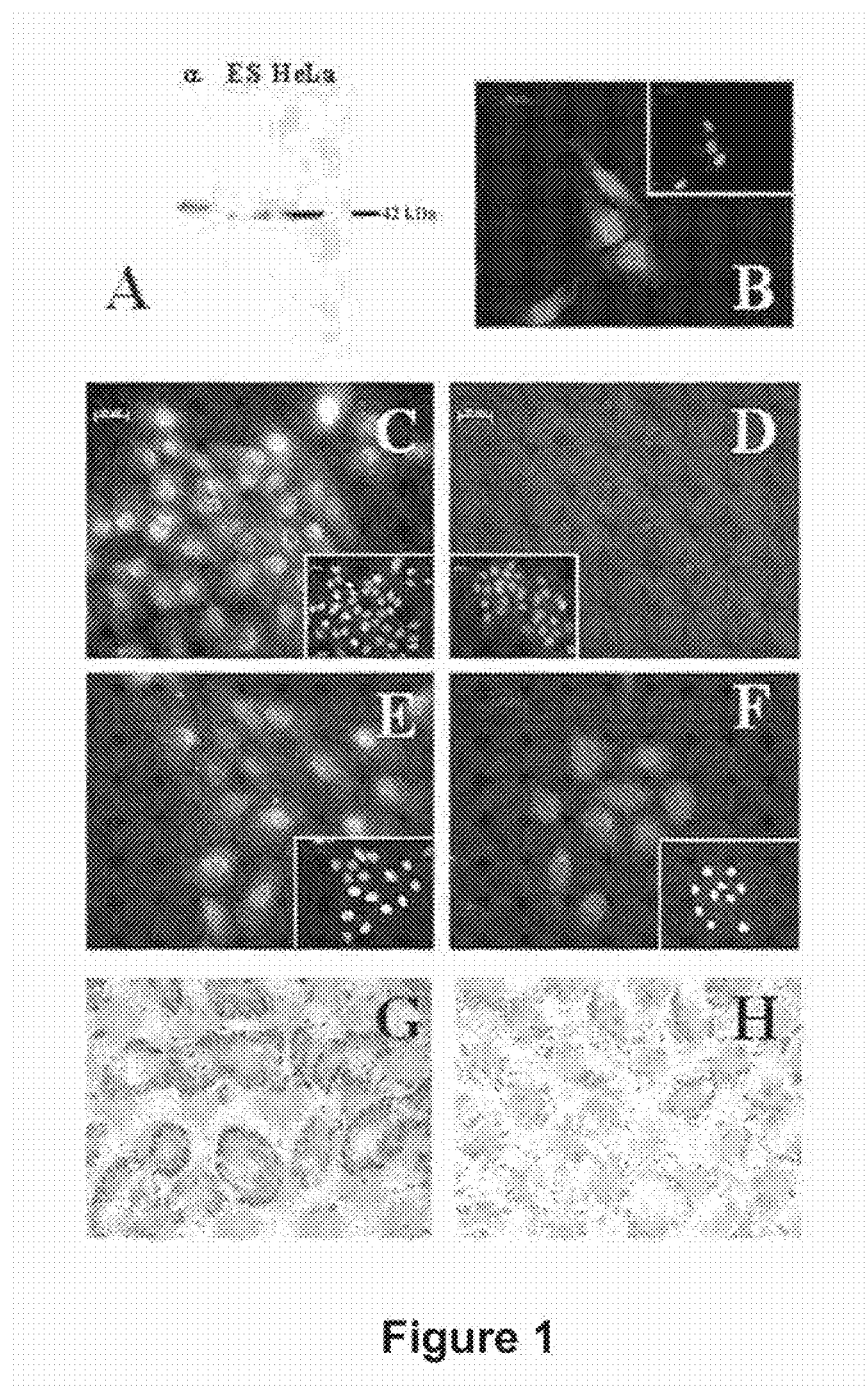

The present application is filed pursuant to 35 U.S.C. 371 as a U.S. National Phase application of International Patent Application No. PCT/EP08/50004, which was filed Jan. 2, 2008, claiming the benefit of priority to European Patent Application No. 07290032.7, which was filed on Jan. 10, 2007. The entire text of the aforementioned applications is incorporated herein by reference in its entirety.

The invention relates to an in vitro method for diagnosing prostate cancer and to antibodies and fragments thereof directed against CK2-α and their use for the diagnosis and prognosis of prostate cancer.

Prostate cancer is a leading cause of illness and death among men in the United States and Western Europe. It represents the most frequent cancer in man up to 50 years of age and the second cause of death due to cancer in western countries. In France, prostate cancer is diagnosed each year in 40,000 men and annually 10,000 deaths are linked to this disease. Despite the use of well established prognostic factors (e.g. Gleason score, TNM classification, Prostate-specific Antigen (PSA) at time of diagnosis) and post-operative pathological stage, some patients will develop PSA relapse or metastatic disease.

There is a lack of accurate markers of clinical outcome, particularly for predicting aggressiveness of prostate carcinoma and in defining high risk patients. Improved prognostic markers are therefore needed to distinguish aggressive tumours from more indolent prostate cancer.

CK2 (formerly known as casein kinase 2 or II) is a ubiquitous protein serine/threonine kinase known to occur as a tetrameric complex of α, α' and β subunits, with an $α_2β_2$ or $αα'β_2$ oligomeric configuration and is localized in both cytosolic and nuclear subcellular compartments (Issinger et al. 1993). CK2 is a multipotential kinase and is reported to phosphorylate many substrates known to play a pivotal role in cell division and differentiation.

CK2 has been implicated in the pathobiology of a variety of processes, ranging from tangle formation in Alzheimer's disease (Masliah et al. 1992) to malignant transformation such as in the prostate (Ahmed et al. 1994), colon (Munstermann et al. 1990), lung carcinomas (Daya Makin et al. 1994) and squamous cell carcinoma of the head and neck (SCCHN) (Gapany et al. 1995).

It was reported that protein kinase CK2 activity was associated with malignant transformation in SCHNN and could serve as a prognostic marker (Gapany et al. 1995 and Faust et al. 1996). Furthermore Faust et al. (1999) used immunohistochemical staining to demonstrate that the catalytic subunit CK2-α was localized predominantly to the nuclei in SCHNN tumours. Therefore, the same authors suggested that immunolocalisation of the catalytic subunit CK2-α could represent an additional tool for prognostic evaluation of patients with SCCHN. Elevated CK2 activity in human breast tumour specimens (Landesman-Bollag et al. 2001) and in head and neck cancers has been reported (Gapany et al. 1995 and Yu et al. 2006). Interestingly, using global gene expression profiling, the CK2-α gene has been identified as a prognostic marker in patients with squamous cell carcinoma of the lung (Oc et al. 2004).

To our knowledge, there are only two published studies using immunohistochemistry for evaluating CK2-α expression in human cancers. One concerned a cohort of 10 head and neck cancers (Faust et al. 1999) and the other investigated CK2-α immunostaining in a limited series of prostate tissue samples (Yenice et al. 1994). However, despite these studies, clinical data dealing with the specific expression of CK2 at the protein level are scarce. Consequently, the prognostic value of CK2 remains uncertain.

Now, the inventors provide the first evidence for a strong association between CK2-α and prostate adenocarcinomas. The inventors have produced a highly specific antibody directed against the CK2-α subunit.

A first object of the invention relates to an in vitro method for diagnosing prostate cancer in a subject, said method comprising measuring the CK2-α level in a prostatic cell obtained from a biological sample of said subject.

A second object of the invention relates to an antibody or a fragment thereof which specifically binds to a CK2-α epitope as set forth in SEQ ID NO:1.

Definitions

A "coding sequence" or a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

As used herein, references to specific proteins (e.g., antibodies or CK2) can include a polypeptide having a native amino acid sequence, as well as variants and modified forms regardless of their origin or mode of preparation. A protein which has a native amino acid sequence is a protein having the same amino acid sequence as obtained from nature (e.g., a naturally occurring CK2) Such native sequence proteins can be isolated from nature or can be prepared using standard recombinant and/or synthetic methods. Native sequence proteins specifically encompass naturally occurring truncated or soluble forms, naturally occurring variant forms (e.g., alternatively spliced forms), naturally occurring allelic variants and forms including post-translational modifications. A native sequence protein includes proteins following post-translational modifications such as glycosylation, or phosphorylation, or other modifications of some amino acid residues.

A "biological sample" encompasses a variety of sample types obtained from a subject and can be used in a diagnostic or monitoring assay. Biological samples include but are not limited to solid tissue samples such as a biopsy specimen or tissue cultures or cells derived therefrom, and the progeny thereof. For example, biological samples include cells obtained from a tissue sample collected from an individual suspected of having a prostate cancer. Therefore, biological samples encompass clinical samples, cells in culture, cell supernatants, cell lysates, and tissue samples. In a preferred embodiment, said biological sample is a transrectal prostate biopsy.

The term "detection" as used herein includes qualitative and/or quantitative detection (measuring levels) with or without reference to a control.

According to the present invention, "antibody" or "immunoglobulin" have the same meaning, and will be used equally in the present invention. In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, trans-placental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. Framework Regions (FRs) refer to amino acid sequences interposed between CDRs.

According to the present invention, the term "diagnosis" encompasses the identification of a disease and the determination of the future course and outcome of a disease.

The term "monoclonal antibody" or "mAb" as used herein refers to an antibody of a single amino acid composition, that is directed against a specific antigen and that is produced by a single clone of B cells or hybridoma.

The term "polyclonal antibody" as used herein refers to an antibody that is directed against a specific antigen that is derived from different B-cell lines.

The term "Fab" denotes an antibody fragment having a molecular weight of about 50,000 Da and antigen binding activity, in which about a half of the N-terminal side of H chain and the entire L chain, among fragments obtained by treating IgG with a protease, papaine, are bound together through a disulfide bond.

The term "F(ab')$_2$" refers to an antibody fragment having a molecular weight of about 100,000 Da and antigen binding activity, which is slightly larger than the Fab bound via a disulfide bond of the hinge region, among fragments obtained by treating IgG with a protease, pepsin.

The term "Fab'" refers to an antibody fragment having a molecular weight of about 50,000 Da and antigen binding activity, which is obtained by cutting a disulfide bond of the hinge region of the F(ab')$_2$.

A single chain Fv ("scFv") polypeptide is a covalently linked VH::VL heterodimer which is usually expressed from a gene fusion including VH and VL encoding genes linked by a peptide-encoding linker. The human scFv fragment of the invention includes CDRs that are held in appropriate conformation, preferably by using gene recombination techniques.

The term "hybridoma" denotes a cell, which is obtained by subjecting a B cell prepared by immunizing a non-human mammal with an antigen to cell fusion with a myeloma cell derived from a mouse or the like which produces a desired monoclonal antibody having an antigen specificity.

The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used.

The term "humanized antibody" refers to antibodies in which the framework or "complementarity determining regions" (CDR) have been modified to comprise the CDR from a donor immunoglobulin of different specificity as compared to that of the parent immunoglobulin. In a preferred embodiment, a mouse CDR is grafted into the framework region of a human antibody to prepare the "humanized antibody".

The term CK2 denotes the casein kinase 2 or II protein, in particular the Human CK2. Protein kinase CK2 is a highly conserved and ubiquitous serine/threonine kinase. Accordingly the term "CK2-α" denotes the CK2-α subunit of CK2. The polypeptide sequence for human CK2-α is deposited in the database under accession number NM_001895.

By "purified" and "isolated" it is meant, when referring to a polypeptide (i.e. the antibody fragment of the invention) or a nucleotide sequence, that the indicated molecule is present in the substantial absence of other biological macromolecules of the same type. The term "purified" as used herein preferably means at least 75% by weight, more preferably at least 85% by weight, more preferably still at least 95% by weight, and most preferably at least 98% by weight, of biological macromolecules of the same type are present. An "isolated" nucleic acid molecule which encodes a particular polypeptide refers to a nucleic acid molecule which is substantially free of other nucleic acid molecules that do not encode the subject polypeptide; however, the molecule may include some additional bases or moieties which do not deleteriously affect the basic characteristics of the composition.

As used herein, the term "subject" denotes a mammal, such as a rodent, a feline, a canine, and a primate. Preferably a subject according to the invention is a human.

Diagnostic Methods

An object of the invention relates to an in vitro method for diagnosing prostate cancer in a subject, said method comprising measuring the CK2-α level in a prostatic cell obtained from a biological sample of said subject.

Typically, the level of CK2-α can be measured by using an antibody or a fragment thereof which specifically binds to CK2-α.

In a preferred embodiment, said antibody or fragment thereof binds to a CK2-α epitope as set forth in SEQ ID NO:1.

In a preferred embodiment, the CK2-α level is measured in the nucleus of said cell.

Typically said biological sample is a prostate biopsy.

In order to monitor the outcome of the cancer, the method of the invention may be repeated at different intervals of time, in order to determine if the CK2-α level increases or decreases, whereby it is determined if the cancer progresses or regresses.

Antibodies and Fragments of the Invention

The inventor have produced a highly specific antibody directed against the CK2-α subunit, and more specifically against to the polypeptide having the sequence VNTHRPREYWDYE (SEQ ID NO:1). Antibodies of the invention are strictly CK2α specific. The sensitivity and selectivity of immunohistochemistry studies performed with such antibodies is far better than the one shown in the Faust paper (1999) using the antibody produced by Goueli et al. (1990).

An aspect of the invention relates to antibody or a fragment thereof which specifically binds to a CK2-α epitope as set forth in SEQ ID NO:1.

The antibodies of the present invention may be monoclonal or polyclonal antibodies, single chain or double chain, chimeric antibodies, or humanized antibodies. Whereas polyclonal antibodies may be used, monoclonal antibodies may be preferred.

Said fragment may be a Fab, F(ab')$_2$, Fab' or scFV fragment.

Antibodies or fragments of the invention can be used in an isolated (e.g., purified) form or contained in a vector, such as a membrane or lipid vesicle (e.g. a liposome).

In a preferred embodiment, antibodies of the invention may be labelled with a detectable molecule or substance, such as a fluorescent molecule, a radioactive molecule or any others labels known in the art. Labels are known in the art that generally provide (either directly or indirectly) a signal.

As used herein, the term "labeled", with regard to the antibody, is intended to encompass direct labeling of the antibody by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody, as well as indirect labeling of the antibody by reactivity with a detectable substance.

An antibody of the invention may be labelled with a radioactive molecule by any method known to the art. For example radioactive molecules include but are not limited radioactive atom for scintigraphic studies such as I123, I124, In111, Re186, Re188. Antibodies of the invention may be also labelled with a spin label for nuclear magnetic resonance (NMR) imaging (also known as magnetic resonance imaging, mri), such as iodine-123, iodine-131, indium-III, fluorine-19, carbon-13, nitrogen-15, oxygen-17, gadolinium, manganese or iron.

Antibodies of the invention may be useful for staging of prostate cancer (e.g., in radioimaging).

An object of the invention relates to a method for detecting CK2-α, said method comprising using an antibody or a fragment thereof which binds to a CK2-α epitope as set forth in SEQ ID NO:1.

A further object of the invention relates to the use of an antibody or a fragment thereof which binds to a CK2-α epitope as set forth in SEQ ID NO:1 for the diagnosis of cancer, especially prostate cancer.

They may be also used alone or in combination with other means for detecting prostate cancer markers, including, but not limited to Prostate Specific Antigen (PSA).

Nucleic Acids, Vectors and Recombinant Host Cells

A further object of the invention relates to a nucleic acid sequence encoding an antibody of the invention or a fragment thereof.

Typically, said nucleic acid is a DNA or RNA molecule, which may be included in any suitable vector, such as a plasmid, cosmid, episome, artificial chromosome, phage or a viral vector.

The terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

So, a further object of the invention relates to a vector comprising a nucleic acid of the invention.

Such vectors may comprise regulatory elements, such as a promoter, enhancer, terminator and the like, to cause or direct expression of said polypeptide upon administration to a subject. Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

Any expression vector for animal cell can be used, so long as a gene encoding the human antibody C region can be inserted and expressed. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vector include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

A further object of the present invention relates to a cell which has been transfected, infected or transformed by a nucleic acid and/or a vector according to the invention.

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

The nucleic acids of the invention may be used to produce a recombinant antibody of the invention in a suitable expression system. The term "expression system" means a host cell and compatible vector under suitable conditions, e.g. for the expression of a protein coded for by foreign DNA carried by the vector and introduced to the host cell.

Common expression systems include *E. coli* host cells and plasmid vectors, insect host cells and Baculovirus vectors, and mammalian host cells and vectors. Other examples of host cells include, without limitation, prokaryotic cells (such as bacteria) and eukaryotic cells (such as yeast cells, mammalian cells, insect cells, plant cells, etc.). Specific examples include *E. coli, Kluyveromyces* or *Saccharomyces* yeasts, mammalian cell lines (e.g., Vero cells, CHO cells, 3T3 cells, COS cells, etc.) as well as primary or established mammalian cell cultures (e.g., produced from lymphoblasts, fibroblasts, embryonic cells, epithelial cells, nervous cells, adipocytes, etc.). Examples also include mouse SP2/0-Ag14 cell (ATCC CRL1581), mouse P3X63-Ag8.653 cell (ATCC CRL1580), CHO cell in which a dihydrofolate reductase gene (hereinafter referred to as "DHFR gene") is defective (Urlaub G et al; 1980), rat YB2/3HL.P2.G11.16Ag.20 cell (ATCC CRL1662, hereinafter referred to as "YB2/0 cell"), and the like.

Methods of Producing Antibodies of the Invention

Antibodies and fragments of the invention may be produced by any technique known in the art, such as, without limitation, any biological, chemical, genetic or enzymatic technique, either alone or in combination.

Procedures for raising polyclonal antibodies are well known. Polyclonal antibodies can be obtained from serum of an animal immunized against the CK2-α epitope as set forth in SEQ ID NO:1, which may be produced by genetic engineering for example according to standard methods well-known by one skilled in the art. Typically, such antibodies can be raised by administering the CK2-α epitope as set forth in SEQ ID NO:1 subcutaneously to New Zealand white rabbits which have first been bled to obtain pre-immune serum. The antigens can be injected at a total volume of 100 μl per site at six different sites. Each injected material may contain adjuvants with or without pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. This and other procedures for raising polyclonal antibodies are disclosed by Harlow et al. (1988), which is hereby incorporated in the references.

Laboratory methods for preparing monoclonal antibodies are well known in the art (see, for example, Harlow et al., 1988). Monoclonal antibodies (mAbs) may be prepared by immunizing against a purified CK2-α epitope as set forth in SEQ ID NO:1 a mammal, e.g. a mouse, rat, human and the like mammals. The antibody-producing cells in the immunized mammal are isolated and fused with myeloma or heteromyeloma cells to produce hybrid cells (hybridoma). The hybridoma cells producing the monoclonal antibodies are utilized as a source of the desired monoclonal antibody. This standard method of hybridoma culture is described in Kohler and Milstein (1975).

Antibody generation techniques not involving immunisation are also contemplated such as for example using phage display technology to examine naive libraries (from non-immunised animals); see Barbas et al. (1992), and Waterhouse et al. (1993).

While mAbs can be produced by hybridoma culture the invention is not to be so limited. For example, knowing the amino acid sequence of the desired sequence, one skilled in the art can readily produce the antibodies, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions. Alternatively, antibodies of the invention can be synthesized by recombinant DNA techniques as is well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

In particular, the invention further relates to a method of producing an antibody or a polypeptide of the invention, which method comprises the steps consisting of: (i) culturing a transformed host cell according to the invention under conditions suitable to allow expression of said antibody or polypeptide; and (ii) recovering the expressed antibody or polypeptide.

Antibodies of the invention are suitably separated from the culture medium by conventional immunoglobulin purification procedures such as, for example, protein A-Sepharose, hydroxylapatite chromatography, gel electrophoresis, dialysis, or affinity chromatography.

In a particular embodiment, the human chimeric antibody of the present invention can be produced by obtaining nucleic sequences encoding VL and VH domains as previously described, constructing a human chimeric antibody expression vector by inserting them into an expression vector for animal cell having genes encoding human antibody CH and human antibody CL, and expressing the coding sequence by introducing the expression vector into an animal cell.

As the CH domain of a human chimeric antibody, it may be any region which belongs to human immunoglobulin, but those of IgG class are suitable and any one of subclasses belonging to IgG class, such as IgG1, IgG2, IgG3 and IgG4, can also be used. Also, as the CL of a human chimeric antibody, it may be any region which belongs to Ig, and those of kappa class or lambda class can be used.

Methods for producing chimeric antibodies involve conventional recombinant DNA and gene transfection techniques are well known in the art (See Morrison S L. et al. (1984) and patent documents U.S. Pat. No. 5,202,238; and U.S. Pat. No. 5,204,244).

The humanized antibody of the present invention may be produced by obtaining nucleic acid sequences encoding CDR domains, as previously described, constructing a humanized antibody expression vector by inserting them into an expression vector for animal cell having genes encoding (i) a heavy chain constant region identical to that of a human antibody and (ii) a light chain constant region identical to that of a human antibody, and expressing the genes by introducing the expression vector into an animal cell.

The humanized antibody expression vector may be either of a type in which a gene encoding an antibody heavy chain and a gene encoding an antibody light chain exists on separate vectors or of a type in which both genes exist on the same vector (tandem type). In respect of easiness of construction of a humanized antibody expression vector, easiness of introduction into animal cells, and balance between the expression levels of antibody H and L chains in animal cells, humanized antibody expression vector of the tandem type is preferred (Shitara K et al. 1994). Examples of tandem type humanized antibody expression vector include pKANTEX93 (WO 97/10354), pEE18 and the like.

Methods for producing humanized antibodies based on conventional recombinant DNA and gene transfection techniques are well known in the art (See, e.g., Riechmann L. et al. 1988; Neuberger M S. et al. 1985). Antibodies can be humanized using a variety of techniques known in the art including, for example, CDR-grafting (EP 239,400; PCT publication WO91/09967; U.S. Pat. Nos. 5,225,539; 5,530,101; and 5,585,089), veneering or resurfacing (EP 592,106; EP 519, 596; Padlan E A (1991); Studnicka G M et al. (1994); Roguska M A. et al. (1994)), and chain shuffling (U.S. Pat. No. 5,565,332). The general recombinant DNA technology for preparation of such antibodies is also known (see European Patent Application EP 125023 and International Patent Application WO 96/02576).

The Fab of the present invention can be obtained by treating an antibody which specifically reacts against the CK2-α epitope as set forth in SEQ ID NO:1 with a protease, papaine. Also, the Fab can be produced by inserting DNA encoding Fab of the antibody into a vector for prokaryotic expression system, or for eukaryotic expression system, and introducing the vector into a procaryote or eucaryote (as appropriate) to express the Fab.

The F(ab')$_2$ of the present invention can be obtained treating an antibody which specifically reacts with the CK2-α epitope as set forth in SEQ ID NO:1 with a protease, pepsin. Also, the F(ab')$_2$ can be produced by binding Fab' described below via a thioether bond or a disulfide bond.

The Fab' of the present invention can be obtained treating F(ab')$_2$ which specifically reacts with the CK2-α epitope as set forth in SEQ ID NO:1 with a reducing agent, dithiothreitol. Also, the Fab' can be produced by inserting DNA encoding Fab' fragment of the antibody into an expression vector for prokaryote, or an expression vector for eukaryote, and introducing the vector into a prokaryote or eukaryote (as appropriate) to perform its expression.

The scFv of the present invention can be produced by obtaining cDNA encoding the VH and VL domains as previously described, constructing DNA encoding scFv, inserting the DNA into an expression vector for prokaryote, or an expression vector for eukaryote, and then introducing the expression vector into a prokaryote or eukaryote (as appropriate) to express the scFv. To generate a humanized scFv fragment, a well known technology called CDR grafting may be used, which involves selecting the complementary determining regions (CDRs) from a donor scFv fragment, and grafting them onto a human scFv fragment framework of known three dimensional structure (see, e.g., WO98/45322; WO 87/02671; U.S. Pat. No. 5,859,205; U.S. Pat. No. 5,585,089; U.S. Pat. No. 4,816,567; EP0173494).

Kits for Diagnosing Cancer

Finally, the invention also provides kits comprising at least one antibody or fragment of the invention. Kits find use in detecting CK2-α expression. Kits of the invention can contain an antibody or a fragment coupled to a solid support, e.g., a tissue culture plate or beads (e.g., sepharose beads). Kits can be provided which contain antibodies for detection and quantification of CK2-α, e.g. in an ELISA or a Western blot. Such antibody useful for detection may be provided with a label such as a fluorescent or radiolabel.

The kit according to the invention is especially adapted for diagnosing prostate cancer.

The invention will further be illustrated in view of the following figures and examples.

FIGURES

FIG. 1: validation of the αCOC antibody:
A: Western blot analysis: α: His-tagged human recombinant CK2α; ES: cellular extract of murine embryonic stem cells; HeLa: cellular extract of HeLa cells. αCOC antibody dilution: 1/1000. B, C, D, E, and F: immunofluorescence analysis on cultured cells: Immunostaining of HeLa cells (B); immunostaining of MCF-10A cells with the antibody solution incubated with GST (C) or GST-CK2α coupled beads (D); immunostaining of MCF-10A cells treated with control siRNA (E) or CK2α siRNA (F). αCOC antibody dilution: 1/500. Small insert: nuclear staining with Hoechst. G and H: immunohistochemical analysis on human prostate adenocarcinoma Immunostaining of a prostate cancer biopsy with the antibody solution incubated with GST (G) or CK2α coupled beads (H). αCOC antibody dilution: 1/500.

Figure 2:
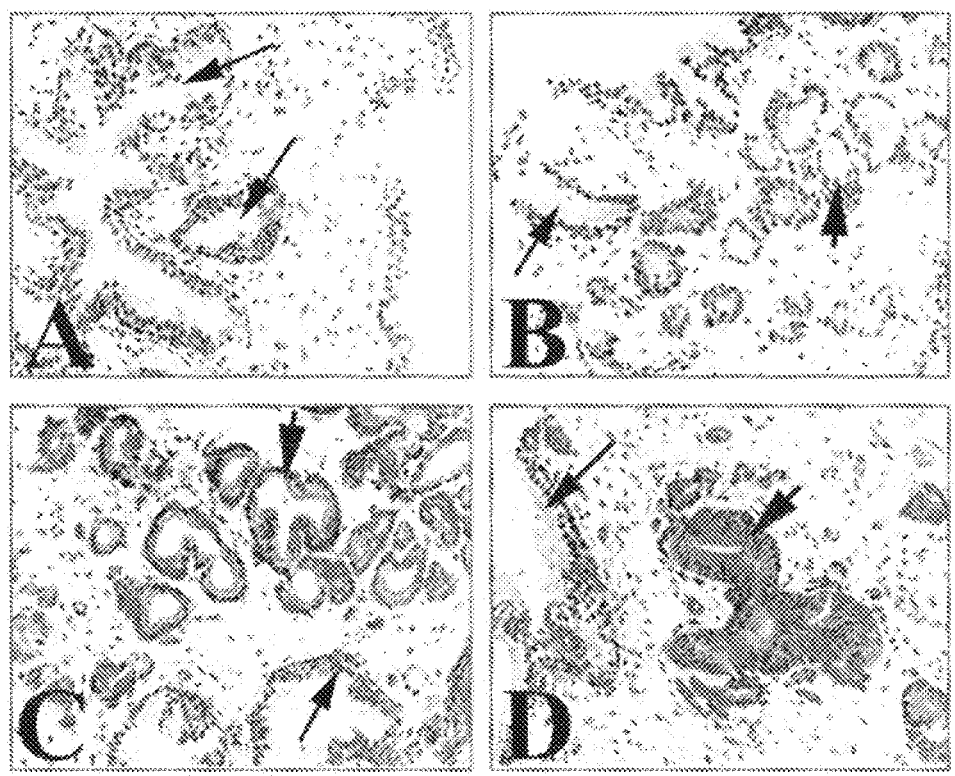

FIG. 2: Expression of CK2α in normal and tumoral prostate biopsies. (A): normal tissue, staining score: 1+; (B): tumoral tissue, staining score: 1+; (C): tumoral tissue, staining score: 2+; (D): tumoral tissue, staining score: 3+. Magnification ×10. Long and short arrows point normal and tumoral glands respectively. Note the mainly cytoplasmic staining of CK2α

Figure 3:
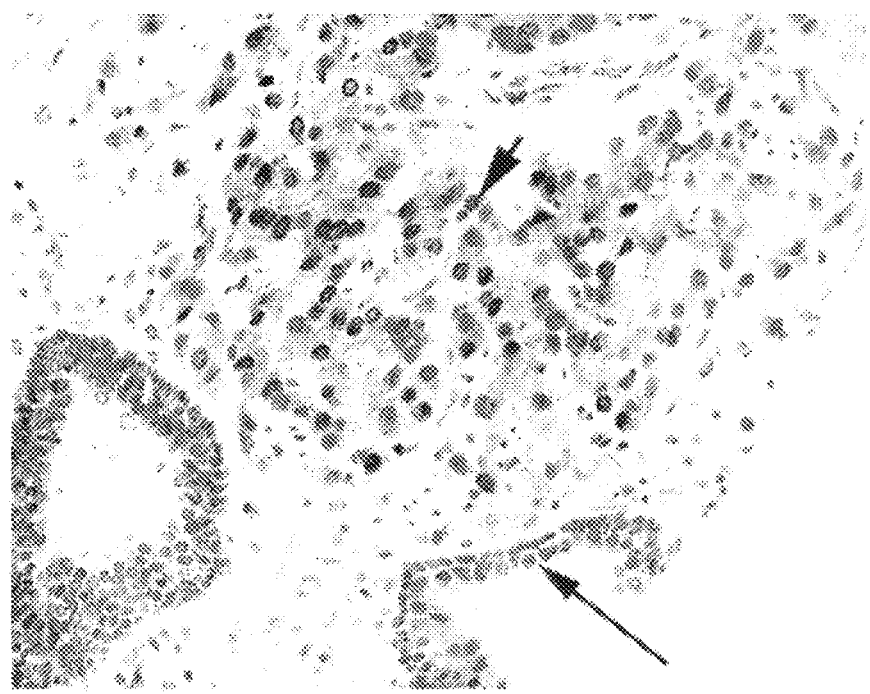

FIG. 3: Example of nuclear CK2α immunostaining in human prostate adenocarcinoma. Total immunostaining score: 5+ (nucleus=3+, cytoplasm=2+). Long and short arrows point to normal and tumoral glands respectively.

EXAMPLE 1

Materials and Methods

Antibodies:
In order to generate antibodies directed against CK2-α subunit we looked to the structural data. The purpose was to create antibodies that will recognize the isolated CK2-α subunit. Four domains in the N-terminal part of the human CK2-α protein were selected to be potential sequences involved in the α-β interaction. The primary sequences, depicted in the table 1 were used to immunize rabbits (Neosystem Strasbourg, France).

TABLE 1

| sequences of epitopes | | |
|---|---|---|
| αCOC antibodies | VNTHRPREYWDYE (15-27) Human CK2α | SEQ ID NO: 1 |
| Beta2 epitope α182 and α 192 antibodies | GKYSEVFEAINIT (48-60) Human CK2 α | SEQ ID NO: 2 |
| Beta 3 epitope α163 and α 205 antibodies | NEKVVVKILKP (62-72) Human CK2 α | SEQ ID NO: 3 |
| β4-β5 Epitope α 286 and α 319 antibodies | IVKDPVSRTPAL (101-112) Human CK2 α | SEQ ID NO: 4 |

These peptides were coupled to KLH (Keyhole Limpet Hemocyanin) protein carrier and injected in 2 rabbits for each peptide.

All the sera were characterized by ELISA and western blot. After sodium sulfate precipitation, antibodies were immuno-affinity purified.

Proteins, Cell Extracts and Western Blotting:
Human recombinant histidine-tagged CK2-α was expressed in *Escherichia Coli* (BL21) and purified at a final concentration of 4 mg/ml. Cell extracts were obtained from HeLa or murine ES cells cultured in DMEM medium. Cells were washed in PBS and lysed in TDG lysis buffer (50 mM Tris-HCl, pH 7.4, 0.5 M NaCl, 0.5%, Triton X-100, 1 mM 4(2-aminoethyl)-benzenesulfonylfluoride (AEBSF), 25 µg/ml each of leupeptin, aprotinin, 1 mM DTT, 2% glycerol. Then, lysates were centrifugated at 14,000×g for 15 min. Proteins were resolved by 12% SDS-PAGE and transferred electrophoretically onto a polyvinylidine difluoride membrane (Roche diagnostic). Residual binding sites on the membranes were blocked for 3 h at 22° C. in PBS buffer containing 0.05% Tween 20 (PBS-T) and 5% powdered skim milk, followed by overnight incubation at 4° C. with the antibody at the indicated dilution in blocking buffer. Membranes were then washed three times with PBS-T and incubated with horseradish peroxidase-labeled anti-rabbit IgG antibody for 1 h at room temperature. The CK2-α expression was revealed with the ECL system (Luminol, PerkinElmer) according to the manufacturer's protocols.

Immunofluorescence:

NIH-3T3 or MCF-10A (ATCC CRL 1658; ATCC CRL-10317) cells were fixed for 20 min in 4% paraformaldehyde and permeabilized for 10 min at 22° C. in PBS buffer, 0.5% Triton X-100. Residual binding sites were blocked with 5% foetal calf serum (FCS) in PBS-T for 1 h at 22° C. Cells were then incubated overnight at 4° C. with primary antibody in blocking buffer. Samples were washed and incubated with Cy3-labeled rabbit secondary antibody for 1 h at 22° C. in the dark and counterstained with Hoechst 33342. Coverslips were mounted with Vectashield (AbCys). Microscopic analysis was performed on Axiovert 200M, using Axiocamâ MRm CCD captor and Axiovision software (Zeiss).

Results:

Specificity of the Anti-CK2-α Antibodies:

The specificity of the αCOC antibody has been demonstrated by (a) its high titer against human recombinant CK2; (b) its ability to recognize human recombinant CK2α by Western blot analysis, (FIG. 1A, first lane), and to detect CK2α 42 kDa protein in cellular extracts of ES or HeLa cells (FIG. 1A, lane 2 and 3, respectively); (c) its ability, but not the preimmune immunoglobulin from the same rabbit to detect CK2α by indirect immunofluorescence on fixed cells (FIG. 1B); (d) the extinction of the immunofluorescence signal upon incubation of the αCOC antibody with recombinant CK2α (FIGS. 1C and 1D); (e) the strong decrease of the immunofluorescence staining in CK2α siRNA-treated cells (FIGS. 1E and 1F); (f) the extinction of the IHC staining upon incubation of the αCOC antibody with recombinant CK2α (FIGS. 1G and 1H).

Taken together, these results showed that the αCOC antibody is specific and useful in ImmunoHistoChemical (IHC) staining of human prostate tissue.

EXAMPLE 2

Nuclear Localization of Protein Kinase CK2 Catalytic Subunit (CK2-α) is Associated with Poor Prognostic Factors in Human Prostate Cancer Materials and Methods Antibody:

The polyclonal anti-CK2-α antibody (αCOC) has been obtained by immunization of New Zealand White rabbits against a 13 amino-acid peptide coupled to Keyhole limpet hemocyanin (see EXAMPLE 1). This peptide corresponds to a part of the N-terminal region of human CK2-α (sequence: VNTHRPREYWDYE).

Proteins, Cell Extracts and Western Blotting:

Human recombinant histidine-tagged CK2-α was expressed in *Escherichia Coli* (BL21) and purified at a final concentration of 4 mg/ml. Cell extracts were obtained from HeLa or murine ES cells cultured in DMEM medium. Cells were washed in PBS and lysed in TDG lysis buffer (50 mM Tris-HCl, pH 7.4, 0.5 M NaCl, 0.5%, Triton X-100, 1 mM 4(2-aminoethyl)-benzenesulfonylfluoride (AEBSF), 25 µg/ml each of leupeptin, aprotinin, 1 mM DTT, 2% glycerol. Then, lysates were centrifugated at 14,000×g for 15 min. Proteins were resolved by 12% SDS-PAGE and transferred electrophoretically onto a polyvinylidine difluoride membrane (Roche diagnostic). Residual binding sites on the membranes were blocked for 3 h at 22° C. in PBS buffer containing 0.05% Tween 20 (PBS-T) and 5% powdered skim milk, followed by overnight incubation at 4° C. with the αCOC antibody at a 1/1000 dilution in blocking buffer. Membranes were then washed three times with PBS-T and incubated with horseradish peroxidase-labeled anti-rabbit IgG antibody for 1 h at room temperature. The CK2-α expression was revealed with the ECL system (Luminol, PerkinElmer) according to the manufacturer's protocols.

siRNA:

Knockdown of CK2-α expression was performed with siRNA purchased from Upstate Cell Signaling (CSNK2A1 smart pool). NIH3T3 or MCF10A cells were cultured on coverslips in 24-well plates and transfected at 30-40% confluence by adding Oligofectamine (Invitrogen) complexed with siRNA (final 22.7 nM). After 72 h, the efficiency of transfection was determined by immunoblot, yielding >60% down-modulation of CK2-α.

Immunofluorescence:

Control or siRNA-treated NIH-3T3 or MCF-10A cells were fixed for 20 min in 4% paraformaldehyde and permeabilized for 10 min at 22° C. in PBS buffer, 0.5% Triton X-100. Residual binding sites were blocked with 5% foetal calf serum (FCS) in PBS-T for 1 h at 22° C. Cells were then incubated overnight at 4° C. with primary αCOC antibody in blocking buffer. Samples were washed and incubated with Cy3-labeled rabbit secondary antibody for 1 h at 22° C. in the dark and counterstained with Hoechst 33342. Coverslips were mounted with Vectashield (AbCys). Microscopic analysis was performed on Axiovert 200M, using Axiocamâ MRm CCD captor and Axiovisionâ software (Zeiss).

Immunohistochemistry:

Prostate biopsies were fixed in AFA buffer (75% alcohol, 2% formol, 5% acetic acid, 18% pure water) and included in paraffin. Sections of 3 µm were cut with a microtome (Microm®) and mounted on poly-L-lysine-coated slides. After deparaffinization in xylene, the sections were rehydratated in graded alcohols. Endogenous peroxydase was quenched at room temperature in perhydrol buffer containing 2% methanol. Antigen retrieval was obtained by diving slides for 2 min in a 95° C. solution of 0.01M sodium citrate buffer pH 6.0. Slides were then processed with a semi-automatic revelation system (Coverplate®), using a revelation kit (Histostain Plus®, Zymed) containing a blocking solution, a multi-species second antibody and an enzymatic complex. The primary rabbit αCOC polyclonal antibody was applied for 1 h at 22° C. at a 1/500 dilution. Detection was accomplished with the AEC Vector® kit (Abcys), following manufacturer's instructions. Identical sections stained in the absence of the primary antibody were used as negative controls. Semiquantitative assessment of antibody staining of the slides was graded using the following score: 0=no staining; 1+=weak staining; 2+=moderate staining; 3+=strong staining. Nuclear and cytoplasmic stainings were both scored, as well as normal glands (if present), as an internal control. The overall score for each sample represents a consensus of scores by two of us (DP and ML), who were blinded to all clinico-pathological variables.

Patients:

Prostate biopsies were performed at the Grenoble University Hospital's Urology Department during the 2003-2004 period. Samples were excluded of the study if there were (i) a lack of material (tumour less than 1 mm or present in just one core), (ii) a diagnosis other than adenocarcinoma (neuro-endocrine tumour, benign adenoma, prostate infection). In total, 131 men were identified using database of the Grenoble University Hospital's Anatomopathology Laboratory. For each patient, a single biopsy (the most representative) was analysed. The clinical and pathological information and prognostic factors about prostate cancer samples were collected in the patient database.

Statistical Analysis:

The associations between the categorical variables were assessed by means of the $\chi_2$ tests. The 95% CIs for significance were estimated, and a p<0.05 was considered to be statistically significant.

Results

Immunohistochemistry of Prostatic Glandular Epithelium:

To take into account the ubiquitous and nucleo-cytoplasmic distribution of CK2-α, nuclear and cytoplasmic staining have been both scored, in normal and malignant prostatic cells. Intensity of staining ranges from 0 to 3+, and sum of the two scores represents the total level of CK2-α expression. For example, a patient sample with 1+ in the nucleus and 3+ in the cytoplasm has a total of 4+. Different representative patterns are showed in FIGS. 2 and 3.

CK2-α is Overexpressed in Malignant Prostate Glandular Cells:

Patient specimens in this study were obtained at the Grenoble University Hospital during 2003 and 2004. One hundred seventy patients were identified, but 39 have been excluded for reasons described in Materials and Methods. A total of 131 patients (i.e. 131 different biopsies) have been analyzed for CK2-α expression and localization. Clinicopathological characteristics of the 131 patients are collected in Table 2.

TABLE 2

Clinicopathological characteristics of the 131 patients

| | |
|---|---|
| Median age | 70 (51-93) |
| Median PSA (ng/ml) (n = 104) | 12.3 (1.8-10400) |
| Gleason score (n = 131) (%) | |
| ≤6 | 60 (45.8) |
| ≥7 | 71 (54.2) |
| cTNM staging (n = 131)(%) | |
| cT1c | 61 (46) |
| cT2 | 43 (33) |
| cT3-T4 | 24 (18.6) |
| cTx | 3 (2.4) |
| M1 | 8 |
| Lymphatic/perineural invasion (n = 131) (%) | |
| Absent | 68 (51.9) |
| Present | 63 (48.1) |
| Tumoral glands present | 131 |
| Normal glands present | 111 |

Noteworthy, 111 samples showed normal prostatic glands adjacent to carcinoma. They were used as internal controls, to evaluate expression level and localization of CK2-α in normal tissue. CK2-α is mainly expressed in the cytoplasm both in normal and in tumour cells. For example, in tumoral glands, mean IHC staining scores are 1.39 (CI95=1.26-1.52) and 0.56 (CI95=0.43-0.69) in the nucleus and the cytoplasm, respectively (p<0.001). Results are similar in normal glands (data not shown). Moreover, IHC staining of prostatic tissue samples clearly showed that although the level of CK2-α differs considerably between individual tissues, the kinase is consistently over-expressed in malignant prostate glandular cells. Mean total IHC staining scores (i.e. nuclear score plus cytoplasm score) are 1.95 (CI95=1.76-2.14) and 0.8 (CI95=0.65-0.95), in malignant and normal prostate glandular cells respectively (p<0.001). These data support the hypothesis that CK2 is conspicuously overexpressed in prostate cancer.

Nuclear Localization of CK2-α is Correlated with High-Grade Tumours:

To examine whether CK2-α expression is associated with a particular disease phenotype, we first determined the relationship between levels of CK2-α expression and established prognostic factors (i.e. initial PSA, Gleason score, initial cTNM classification, lymphatic or perineural invasion). Total or cytoplasmic IHC staining scores show no significant correlation with any of these factors (see tables 3 and 4):

TABLE 3

Relationship between prognostic factors and total CK2α immunostaining score (0/1+, 2 , 3+ or more).

| | 0/1+ (n = 54) | 2+ (n = 40) | 3+ (n = 37) | |
|---|---|---|---|---|
| Gleason score (%) | | | | |
| ≤6 | 33 (61) | 15 (37.5) | 12 (32.4) | (0/1+ vs 2+ p = 0.023) |
| ≥7 | 21 (39) | 25 (62.5) | 25 (67.6) | (2+ vs 3+ p = 0.64) (0/1+ vs 3+ p = 0.0072) |
| cTNM staging (%) (Tx excluded) | | | | |
| cT1c | 30 (58.8) | 17 (42.5) | 14 (38.9) | (0/1+ vs 2+ p = 0.15) |
| cT2 | 17 (33.3) | 15 (37.5.9) | 11 (30.5) | (2+ vs 3+ p = 0.55) |
| cT3-T4 | 4 (7.9) | 8 (20) | 11 (30.5) | (0/1+ vs 3+ p = 0.017) |
| Lymphatic/perineural invasion (%) | | | | |
| Absent | 34 (62.9) | 22 (40.7) | 18 (43.2) | (0/1+ vs 2+ p = 0.083) |
| Present | 20 (37.1) | 32 (59.3) | 22 (56.8) | (2+ vs 3+ p = 0.87) (0/1+ vs 3+ p = 0.63) |

TABLE 4

Relationship between prognostic factors and cytoplasmic CK2α immunostaining score (0/1+ or 2+ /3+).

| | 0/1+ (n = 54) | 2+/3+ (n = 40) | |
|---|---|---|---|
| Gleason score (%) | | | |
| ≤6 | 38 (46.9) | 22 (44) | (p = 0.74) |
| ≥7 | 43 (53.1) | 28 (56) | |
| cTNM staging (%) (Tx excluded) | | | |
| cT1c | 39 (51.3) | 22 (44) | (p = 0.39) |
| cT2 | 26 (34.2) | 16 (32) | |
| cT3-T4 | 11 (14.5) | 12 (24) | |
| Lymphatic/perineural invasion (%) | | | |
| Absent | 38 (47) | 25 (50) | (p = 0.73) |
| Present | 43 (53) | 25 (50) | |

However, we noticed the presence of CK2-α in the nucleus in a subset of prostate cancers. Patients were therefore stratified into those with no nuclear staining in tumour cells (group Nuc−, n=77, 58.7%), and those with a nuclear staining score of 1+ or more (group Nuc+, n=54, 41.3%). In this last subset of patients, 38 (70.4%) have a Gleason score of 7 or more, as compared with 33 (42.9%) in group Nuc−($X_2$ test, p=0.0019). A positive correlation of nuclear positive target cells with the cT stages has also been identified: in 52 evaluable Nuc+ patients, 23 (44.3%), 14 (26.9%) and 15 (28.8%) have a cT1c, cT2 and cT3-T4 disease respectively. In 76 evaluable Nuc− patients, 38 (50%), 29 (38.1%) and 9 (11.9%) have a cT1c, cT2 and cT3-T4 tumour grade respectively. This difference is statistically significant ($X_2$ test, p=0.046). Patients with lymph node invasion or metastasis were under-represented, so there are no statistically significant differences between the Nuc− and Nuc+ subgroups for these two items. However, Nuc+ patients have more locally aggressive tumours: 32 (59.3%) have lymphatic or perineural invasion, as compared with 31 Nuc− patients (40.3%, $X_2$ test, p=0.032). Thus, increased nuclear staining of CK2-α in a subset of prostate cancers strongly correlated with poor prognostic factors. A differential nuclear staining was also observed on the basis of initial PSA. Median and mean initial PSA are 8.9 ng/ml (1.8-1500) and 466.08 ng/ml (CI95=57.78-874.11) in Nuc+ patients and 27.45 ng/ml (2.5-10400) and 57.48 ng/ml (CI95=10.83-104.13) in Nuc− patients respectively. Despite a strong trend, these differences are not statistically significant. Characteristics and results are collected in table 5:

TABLE 5

Characteristics and prognostic factors in Nuc− and Nuc+ patients

|  | Nuc⁻ (n = 77) | Nuc⁺ (n = 54) |  |
|---|---|---|---|
| Median age | 69 (52-88) | 72 (51-93) |  |
| Median PSA (ng/ml) | 8.9 (1.8-1500) | 27.5 (2.5-10400) |  |
| Gleason score (%) |  |  |  |
| ≤6 | 44 (57.1) | 16 (29.6) | (p = 0.019) |
| ≥7 | 33 (42.9) | 38 (70.4) |  |
| cTNM staging (%) (Tx excluded) |  |  |  |
| cT1c | 38 (50) | 23 (44.3) | (p = 0.046) |
| cT2 | 29 (38.1) | 14 (26.9) |  |
| cT3-T4 | 9 (11.9) | 15 (28.8) |  |
| Lymphatic/perineural invasion (%) |  |  |  |
| Absent | 46 (59.7) | 22 (40.7) | (p = 0.032) |
| Present | 31 (40.3) | 32 (59.3) |  |

Due to lack of sufficient follow-up, survival data have not been generated.

Discussion:

The first evidence has been provided for a strong association between a nuclear localization of CK2-α, evaluated by immunohistochemistry, and poor prognostic factors in a retrospective cohort of 131 human prostate adenocarcinomas. The inventors have produced a highly specific antibody directed against the CK2-α subunit. The anti-CK2-α polyclonal antibody used in our study to evaluate the expression and the localization of CK2-α in prostate cancer biopsies shows a strong specificity for CK2-α in Western blot as well as in immunofluorescence and IHC analysis.

It has been demonstrated therewith that nuclear CK2-α localization is significantly correlated with higher Gleason score, more locally advanced disease (cT3-T4) and more perineural or lymphatic invasion. Thus, the results indicate that said antibody is a promising tool for the diagnosis of cancer, in particular prostate cancer.

Transrectal prostate biopsies are interesting, because in most of them, normal prostatic glandular epithelium is also present allowing easy comparison between tumour and normal tissue. Globally, IHC staining pattern for CK2-α in prostate biopsies shows a nucleo-cytoplasmic distribution, consistent with other findings (Yenice et al. 1994), and appears highly heterogeneous in different patient samples. In most prostate cancers, CK2-α is overexpressed predominantly in the cytoplasm but this cytoplasmic staining does not correlate with respect to the stage of disease or degree of tumour differentiation. By contrast, and interestingly, patients with CK2-α nuclear staining (even weak) have high-grade and poorly differentiated tumour (Gleason score ≥7), more locally aggressive tumour (cT3-4) and more potential capsular involvement (lymphatic or perineural invasion). Initial PSA tends to be higher in Nuc+ patients, but differences are not statistically significant. Collectively, our data support the notion that the nuclear localization of CK2-α is an adverse prognostic marker in this pathology.

Taken together, these data implicate CK2 in prostate cancer progression and our observations provided the first evidence for a strong correlation between CK2-α expression pattern and tumour aggressiveness. Therefore CK2 can be used to predict clinical outcome, especially in clinically localized prostate cancer. In this situation, pretreatment nomograms with clinical (cT), histological (Gleason score) and biological (initial PSA) parameters are widely used, but none of them include biomarkers (D'Amico et al. 1999 and Ross et al. 2001). In other cancers, such biomarkers are now well established, fostering changes in disease's management (e.g. c-erbB2 in breast cancer).

References

Ahmad K A, Wang G, Slaton J, Unger G, Ahmed K. Targeting CK2 for cancer therapy. Anticancer Drugs 2005; 16(10): 1037-43.

Ahmed K, Gerber D A, Cochet C. Joining the cell survival squad: an emerging role for protein kinase CK2. Trends Cell Biol 2002; 12(5):226-30.

Barbas C F, Bain J D, Hoekstra D M, Lerner R A. (1992), Semisynthetic combinatorial antibody libraries: a chemical solution to the diversity problem. PNAS USA, 89, 4457-4461

Brady G, Jantzen H M, Bernard H U, Brown R, Schutz G, Hashimoto-Gotoh T. New cosmid vectors developed for eukaryotic DNA cloning. Gene. 1984 February; 27(2):223-32.

Buchou T, Vernet M, Blond O, Jensen H H, Pointu H, Olsen B B, et al. Disruption of the regulatory beta subunit of protein kinase CK2 in mice leads to a cell-autonomous defect and early embryonic lethality. Mol Cell Biol 2003; 23(3):908-15.

D'Amico A V, Whittington R, Malkowicz S B, Fondurulia J, Chen M H, Kaplan I, et al. Pretreatment nomogram for prostate-specific antigen recurrence after radical prostatectomy or external-beam radiation therapy for clinically localized prostate cancer. J Clin Oncol 1999; 17(1):168-72.

Daya-Makin M, Sanghera J S, Mogentale T L, Lipp M, Parchomchuk J, Hogg J C, Pelech S L. Activation of a tumor-associated protein kinase (p40TAK) and casein kinase 2 in human squamous cell carcinomas and adenocarcinomas of the lung. Cancer Res. 1994 Apr. 15; 54(8):2262-8.

Faust R A, Gapany M, Tristani P, Davis A, Adams G L, Ahmed K. Elevated protein kinase CK2 activity in chromatin of head and neck tumors: association with malignant transformation. Cancer Lett. 1996 Mar. 19; 101(1):31-5.

Faust R A, Niehans G, Gapany M, Hoistad D, Knapp D, Cherwitz D, et al. Subcellular immunolocalization of protein kinase CK2 in normal and carcinoma cells. Int J Biochem Cell Biol 1999; 31(9):941-9.

Filhol O, Martiel J L, Cochet C. Protein kinase CK2: a new view of an old molecular complex. EMBO Rep 2004; 5(4):351-5.

Filhol O, Nueda A, Martel V, Gerber-Scokaert D, Benitez M J, Souchier C, et al. Live-cell fluorescence imaging reveals the dynamics of protein kinase CK2 individual subunits. Mol Cell Biol 2003; 23(3):975-87.

Gapany M, Faust R A, Tawfic S, Davis A, Adams G L, Ahmed K. Association of elevated protein kinase CK2 activity with aggressive behavior of squamous cell carcinoma of the head and neck. Mol Med 1995; 1(6):659-66.

Gillies S D, Morrison S L, Oi V T, Tonegawa S. A tissue-specific transcription enhancer element is located in the major intron of a rearranged immunoglobulin heavy chain gene. Cell. 1983 July; 33(3):717-28.

Guerra B, Issinger O G. Protein kinase CK2 and its role in cellular proliferation, development and pathology. Electrophoresis 1999; 20(2):391-408.

Harlow E. et al., Antibodies: A Laboratory Manual, Cold Spring Harbor Laboratory, New York, (1988)

Issinger O G. Casein kinases: pleiotropic mediators of cellular regulation. Pharmacol Ther 1993; 59(1):1-30.

Izeradjene K, Douglas L, Delaney A, Houghton J A. Casein kinase II (CK2) enhances death-inducing signaling complex (DISC) activity in TRAIL-induced apoptosis in human colon carcinoma cell lines. Oncogene 2005; 24(12):2050-8.

Kohler and Milstein (1975) Continuous cultures of fused cells secreting antibody of predefined specificity. Nature; 256, 495-7

Kuwana Y, Asakura Y, Utsunomiya N, Nakanishi M, Arata Y, Itoh S, Nagase F, Kurosawa Y. Expression of chimeric receptor composed of immunoglobulin-derived V regions and T-cell receptor-derived C regions. Biochem Biophys Res Commun. 1987 Dec. 31; 149(3):960-8.

Landesman-Bollag E, Romieu-Mourez R, Song D H, Sonenshein G E, Cardiff R D, Seldin D C. Protein kinase CK2 in mammary gland tumorigenesis. Oncogene 2001; 20(25): 3247-57.

Li X, Guan B, Maghami S, Bieberich C J. NKX3.1 is regulated by protein kinase CK2 in prostate tumor cells. Mol Cell Biol 2006; 26(8):3008-17.

Masliah E, Iimoto D S, Mallory M, Albright T, Hansen L, Saitoh T. Casein kinase II alteration precedes tau accumulation in tangle formation. Am J Pathol. 1992 February; 140(2):263-8.

Mason J O, Williams G T, Neuberger M S. Transcription cell type specificity is conferred by an immunoglobulin VH gene promoter that includes a functional consensus sequence. Cell. 1985 June; 41(2):479-87.

Miyaji H, Mizukami T, Hosoi S, Sato S, Fujiyoshi N, Itoh S. Expression of human beta-interferon in Namalwa KJM-1 which was adapted to serum-free medium. Cytotechnology. 1990 March; 3(2):133-40.

Mizukami T, Itoh S. A new SV40-based vector developed for cDNA expression in animal cells. J Biochem (Tokyo). 1987 May; 101(5):1307-10.

Morrison S L, Johnson M J, Herzenberg L A, Oi V T. Chimeric human antibody molecules: mouse antigen-binding domains with human constant region domains. Proc Natl Acad Sci USA. 1984 November; 81(21):6851-5.

Munstermann U, Fritz G, Seitz G, Lu Y P, Schneider H R, Issinger O G. Casein kinase II is elevated in solid human tumours and rapidly proliferating non-neoplastic tissue. Eur J Biochem. 1990 Apr. 30; 189(2):251-7.

Neuberger M S, Williams G T, Fox R O. Recombinant antibodies possessing novel effector functions. Nature. 1984 Dec. 13-19; 312(5995):604-8.

O'Hare K, Benoist C, Breathnach R. Transformation of mouse fibroblasts to methotrexate resistance by a recombinant plasmid expressing a prokaryotic dihydrofolate reductase. Proc Natl Acad Sci USA. 1981 March; 78(3): 1527-31.

P Oc, Rusch V, Talbot S G, Sarkaria I, Viale A, Socci N, et al. Casein kinase II alpha subunit and C1-inhibitor are independent predictors of outcome in patients with squamous cell carcinoma of the lung. Clin Cancer Res 2004; 10(17): 5792-803.

Padlan E A. A possible procedure for reducing the immunogenicity of antibody variable domains while preserving their ligand-binding properties. Mol Immunol. 1991 April-May; 28(4-5):489-98.

Padmanabha R, Chen-Wu J L, Hanna D E, Glover C V. Isolation, sequencing, and disruption of the yeast CKA2 gene: casein kinase II is essential for viability in *Saccharomyces cerevisiae*. Mol Cell Biol 1990; 10(8):4089-99.

Penner C G, Wang Z, Litchfield D W. Expression and localization of epitope-tagged protein kinase CK2. J Cell Biochem 1997; 64(4):525-37.

Pinna L A, Meggio F. Protein kinase CK2 ("casein kinase-2") and its implication in cell division and proliferation. Prog Cell Cycle Res 1997; 3:77-97.

Ravi R, Bedi A. Sensitization of tumor cells to Apo2 ligand/TRAIL-induced apoptosis by inhibition of casein kinase II. Cancer Res 2002; 62(15):4180-5.

Riechmann L, Clark M, Waldmann H, Winter G Reshaping human antibodies for therapy. Nature. 1988 Mar. 24; 332 (6162):323-7.

Roguska M A, Pedersen J T, Keddy C A, Henry A H, Searle S J, Lambert J M, Goldmacher V S, Blattler W A, Rees A R, Guild B C. Humanization of murine monoclonal antibodies through variable domain resurfacing. Proc Natl Acad Sci USA. 1994 Feb. 1; 91(3):969-73.

Ross P L, Scardino P T, Kattan M W. A catalog of prostate cancer nomograms. J Urol 2001; 165(5):1562-8.

Scaglioni P P, Yung T M, Cai L F, Erdjument-Bromage H, Kaufman A J, Singh B, et al. A CK2-Dependent Mechanism for Degradation of the PML Tumor Suppressor. Cell 2006; 126(2):269-83.

Seldin D C, Leder P. Casein kinase II alpha transgene-induced murine lymphoma: relation to theileriosis in cattle. Science 1995; 267(5199):894-7.

Shin S, Lee Y, Kim W, Ko H, Choi H, Kim K. Caspase-2 primes cancer cells for TRAIL-mediated apoptosis by processing procaspase-8. Embo J 2005; 24(20):3532-42.

Shitara K, Nakamura K, Tokutake-Tanaka Y, Fukushima M, Hanai N. A new vector for the high level expression of chimeric antibodies in myeloma cells. J Immunol Methods. 1994 Jan. 3; 167(1-2):271-8.

Slaton J W, Unger G M, Sloper D T, Davis A T, Ahmed K. Induction of apoptosis by antisense CK2 in human prostate cancer xenograft model. Mol Cancer Res 2004; 2(12):712-21.

Stalter G, Siemer S, Becht E, Ziegler M, Remberger K, Issinger O G. Asymmetric expression of protein kinase CK2 subunits in human kidney tumors. Biochem Biophys Res Commun 1994; 202(1):141-7.

Studnicka G M, Soares S, Better M, Williams R E, Nadell R, Horwitz A H. Human-engineered monoclonal antibodies retain full specific binding activity by preserving non-CDR complementarity-modulating residues. Protein Eng. 1994 June; 7(6):805-14.

Tawfic S, Yu S, Wang H, Faust R, Davis A, Ahmed K. Protein kinase CK2 signal in neoplasia. Histol Histopathol 2001; 16(2):573-82.

Urlaub G, Chasin L A. Isolation of Chinese hamster cell mutants deficient in dihydrofolate reductase activity. Proc Natl Acad Sci USA. 1980 July; 77(7):4216-20.

Wang G, Ahmad K A, Unger G, Slaton J W, Ahmed K. CK2 signaling in androgen-dependent and -independent prostate cancer. J Cell Biochem 2006.

Wang G, Unger G, Ahmad K A, Slaton J W, Ahmed K. Downregulation of CK2 induces apoptosis in cancer cells—a potential approach to cancer therapy. Mol Cell Biochem 2005; 274(1-2):77-84.

Waterhouse P, Griffiths A D, Johnson K S, Winter G. (1993) Combinatorial infection and in vivo recombination: a strategy for making large phage antibody repertoires. Nucleic Acids Research, 21, 2265-2266

Yenice S, Davis A T, Goueli S A, Akdas A, Limas C, Ahmed K. Nuclear casein kinase 2 (CK-2) activity in human normal, benign hyperplastic, and cancerous prostate. Prostate 1994; 24(1):11-6.

Yu M, Yeh J, Van Waes C. Protein kinase casein kinase 2 mediates inhibitor-kappaB kinase and aberrant nuclear factor-kappaB activation by serum factor(s) in head and neck squamous carcinoma cells. Cancer Res 2006; 66(13): 6722-31.

The invention claimed is:

1. An isolated antibody or antigen-binding fragment thereof which specifically binds to a CK2-α epitope as set forth in SEQ ID NO:1.

2. The isolated antibody or antigen-binding fragment thereof of claim 1, wherein the isolated antibody or antigen-binding fragment thereof is monoclonal or polyclonal.

3. The isolated antibody or antigen-binding fragment thereof according to claim 1, wherein the isolated antibody or antigen-binding fragment thereof is labeled with a detectable molecule or substance.

4. A kit for diagnosing cancer, comprising an isolated antibody or antigen-binding fragment thereof which specifically binds to a CK2-α epitope as set forth in SEQ ID NO:1.

5. An in vitro method for diagnosing prostate cancer in a subject, said method comprising measuring the CK2-α level in a prostatic cell obtained from a biological sample of said subject wherein the level of CK2-α is measured by using the isolated antibody or antigen-binding fragment thereof of claim 1.

6. The method according to claim 5, wherein the isolated antibody or antigen-binding fragment thereof binds to a CK2-α epitope as set forth in SEQ ID NO:1.

7. The method according to claim 5, wherein the CK2-α level is measured in the nucleus of said cell.

8. The method according to claim 5, wherein said biological sample is a prostate biopsy.

9. A method for detecting CK2-α, said method comprising using the isolated antibody or antigen-binding fragment thereof according to claim 1.

10. A method for diagnosing cancer, said method comprising the step of using the isolated antibody or antigen-binding fragment thereof according to claim 1.

* * * * *

SEQUENCE LISTING

```
<160> NUMBER OF SEQ ID NOS: 4

<210> SEQ ID NO 1
<211> LENGTH: 13
<212> TYPE: PRT
<213> ORGANISM: Artificial
<220> FEATURE:
<223> OTHER INFORMATION: Epitope

<400> SEQUENCE: 1

Val Asn Thr His Arg Pro Arg Glu Tyr Trp Asp Tyr Glu
1               5                   10

<210> SEQ ID NO 2
<211> LENGTH: 13
<212> TYPE: PRT
<213> ORGANISM: Artificial
<220> FEATURE:
<223> OTHER INFORMATION: Epitope

<400> SEQUENCE: 2

Gly Lys Tyr Ser Glu Val Phe Glu Ala Ile Asn Ile Thr
1               5                   10

<210> SEQ ID NO 3
<211> LENGTH: 11
<212> TYPE: PRT
<213> ORGANISM: Artificial
<220> FEATURE:
<223> OTHER INFORMATION: Epitope

<400> SEQUENCE: 3

Asn Glu Lys Val Val Val Lys Ile Leu Lys Pro
1               5                   10

<210> SEQ ID NO 4
<211> LENGTH: 12
<212> TYPE: PRT
<213> ORGANISM: Artificial
<220> FEATURE:
<223> OTHER INFORMATION: Epitope

<400> SEQUENCE: 4

Ile Val Lys Asp Pro Val Ser Arg Thr Pro Ala Leu
1               5                   10
```